United States Patent [19]

Bouillon et al.

[11] 3,950,532

[45] Apr. 13, 1976

[54] TOPICAL APPLICATION OF CIS OF TRANS 3,4-THIOLANEDIOL TO REDUCE THE GREASY APPEARANCE OF HAIR AND SKIN

[75] Inventors: Claude Bouillon, Eaubonne; Michel Colin, Livry-Gargan, both of France

[73] Assignee: L'Oreal, Paris, France

[22] Filed: May 10, 1972

[21] Appl. No.: 251,884

[30] Foreign Application Priority Data
May 14, 1971   Luxemburg.............................. 63168

[52] U.S. Cl. .................... 424/275; 8/10.2; 252/106; 260/332.1; 260/332.3 R; 424/DIG. 1; 424/DIG. 2; 424/DIG. 4; 424/45; 424/47; 424/63; 424/70; 424/71; 424/72; 424/78; 424/86; 424/81; 424/362; 424/31

[51] Int. Cl.² ....................................... A61K 31/38
[58] Field of Search ................. 260/332.1, 332.3 R; 424/275, DIG. 4; 252/106, 107

[56] References Cited
UNITED STATES PATENTS

| | | |
|---|---|---|
| 2,400,436 | 5/1946 | Patterson et al............. 260/332.3 R |
| 3,098,793 | 7/1963 | Loev................................ 424/275 X |
| 3,236,733 | 2/1966 | Karsten et al....................... 424/263 |
| 3,564,095 | 2/1971 | Sarett et al. ......................... 424/275 |

OTHER PUBLICATIONS

Weinberg et al., Tetrahedron, Vol. 24, Aug. 1968, pp. 5415 to 5417.

*Primary Examiner*—Jerome D. Goldberg
*Assistant Examiner*—Vera C. Clark
*Attorney, Agent, or Firm*—Cushman, Darby & Cushman

[57] ABSTRACT

A composition and method for treating the hair and skin characterized by a greasy, unaesthetic appearance to reduce or essentially eliminate this greasy appearance which includes topically applying to a human having hair or skin so characterized a cosmetic composition containing as an active ingredient a cis or trans 3,4-thiolannediol, its cis or trans S-oxide derivatives or its cis or trans S-dioxide derivatives.

12 Claims, No Drawings

TOPICAL APPLICATION OF CIS OF TRANS 3,4-THIOLANEDIOL TO REDUCE THE GREASY APPEARANCE OF HAIR AND SKIN

The present invention relates to cosmetic compositions which when administered orally or topically to a human being having hair, skin or scalp characterized by a greasy and unaesthetic appearance, significantly improves the condition and appearance of the hair, scalp and skin by essentially eliminating this greasy and unaesthetic appearance. The composition of the present invention is also usefully employed to combat dandruff. The compositions of the present invention comprise a suitable cosmetic vehicle and at least one active compound of the formula

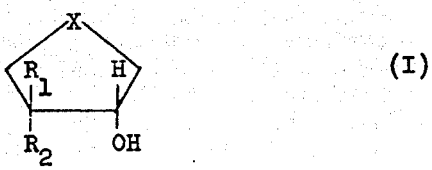

wherein
X is selected from the group consisting of S, SO and $SO_2$,
$R_1$ is selected from the group consisting of H, in which case $R_2$ is OH, and OH, in which case $R_2$ is H.

The active compounds used in the compositions of the present invention are known, per se, but not until the present invention have their excellent cosmetic properties been recognized.

More particularly, the present invention relates to a cosmetic composition utilizing as the active component a member selected from the group consisting of
cis and trans 3,4-thiolannediol,
cis and trans 3,4-thiolannediol S-oxide, and
cis and trans 3,4-thiolannediol S-dioxide.

As indicated above, these compounds are known compounds, the preparation of which is described in certain documents such as "Chemical Communications" 1969, page 171; Coll. Czech Chem. Comm. 1965, 30, 1158; and J. Biol. Chem. 1942 (145) 495.

The preparation of the above active compounds having a trans structure is obtained by starting with DL-1,4-dihalogeno 2,3-butanediol, or again from dimethane sulfonates or di-p-toluenesulfonates of 2,3-dihydroxy 1,4-butylene. On the other hand, the above active compounds of cis structure are obtained from these same initial reactants having instead a meso structure.

The operating conditions employed to obtain cis or trans 3,4-thiolannediol are identical and comprise reacting the meso or DL derivative, respectively, of the above mentioned initial reactant compounds in an aqueous, alcoholic or dilute aqueous alcoholic solution with an alkali metal or alkaline earth sulfice or alternatively with a mixture of an alkali metal or alkaline earth sulfhydrate and sulfide.

The reaction is generally carried out at a temperature of 15° to 100°C and preferably between 20° and 50°C.

The corresponding cis and trans sulfoxides are prepared from the resulting cis and trans 3,4-thiolannediol by the action of hydrogen peroxide, to which, optionally, there can be added acetic acid or an organic peracid such as perphthalic or perbenzoic, either substituted or not, in a chlorinated or aromatic hydrocarbon. The reaction temperature is generally kept below 50°C and preferably between 0° and 30°C.

The corresponding cis and trans sulfones are prepared either (1) by the action of an alkaline permanganate or an organic peracid or a mixture of hydrogen peroxide or carboxylic acid (preferably formic acid or acetic acid) on 3-sulfolene, or by the action of hydrogen peroxide, to which optionally there can be added acetic acid, or by an organic peracid (such as optionally substituted perbenzoic or perphthalic acid) in a chlorinated or aromatic hydrocarbon, on 3,4-thiolannediol, or again on its corresponding S-oxide derivative. The reaction temperature generally ranges between 50° and 100°C and preferably between 60° and 80°C.

The active compounds that are used in the preparation of the compositions of the present invention exhibit very good solubility, particularly in water and in dilute alcohol solutions. However, it should be noted that the S-oxide and S-dioxide derivatives are slightly less soluble than cis or trans 3,4-thiolannediol.

The compositions according to the present invention can be in various forms and can contain from about 0.5 to 20%, preferably from 1 to 10%, by weight of at least one active compound of Formula I as defined above. Thus, they can be solutions and/or aqueous or dilute alcohol suspensions for use as a lotion for maintenance of the scalp. The low molecular weight alcohols generally used for making such dilute alcohol solutions are ethanol and isopropanol.

The capillary compositions according to the invention can contain the active compounds defined above by Formula I either alone or as mixtures thereof, or again in admixture with other conventional compounds employed to reduce a greasy and unaesthetic appearance of the hair, or again in admixture with bactericidal or fungicidal agents.

The capillary compositions of the present invention can also contain ingredients such as penetration agents or perfumes which are generally used in cosmetic preparations.

The present invention also has for its object a process for treating hair to improve its appearance, a process essentially characterized by the fact that the capillary product as defined above is applied to the hair by massage. The amount of said composition applied to the scalp generally is that amount effective to substantially reduce or eliminate the greasy and unaesthetic appearance of the hair, skin or scalp. Ordinarily, this amount can range between 10 and 20 cc of said composition, although it will be recognized that other amounts can be used depending on such easily determined factors as, for instance, the amount of hair or skin being treated.

the novel compositons according to the present invention can also take the form of hair-setting lacquers or lotions containing at least one active compound as defined in Formula I in a suitable cosmetic vehicle or carrier, together with at least one cosmetic resin having, generally, a molecular weight ranging from about 10,000–70,000.

Representative cosmetic resins that can be used include polyvinylpyrrolidone having a molecular weight ranging from 10,000–70,000, vinylpyrrolidone/vinyl acetate copolymer 70%:30% to 30%:70% (K ethanol 1% 25–50); copolymer of vinyl acetate and an unsaturated carboxylic acid such as crotonic acid (M.W. 20,000); copolymer resulting from the polymerization of vinyl acetate (75–85%), crotonic acid (5–15%) and an acrylic or methacrylic ester (5–15%) or an alkylvinyl ether (5–15%); copolymer resulting from copolymerization of vinyl acetate (63–88%), crotonic acid (5–15%) and (a) a vinyl ester of a long carbon chain acid having 10–22 carbon atoms or (b) an allyl or methallyl ester of a long carbon chain acid having 10–22 carbon atoms (5–25%); copolymer resulting from the copolymerization of an ester derived from an unsaturated alcohol having 2–12 carbon atoms and a saturated short chain carboxylic acid having 2–5 carbon atoms (65–80%) and a short carbon chain, unsaturated acid having 4–20 carbon atoms (7–12%) and at least one ester derived from a short chain saturated alcohol having 8–18 carbon atoms and an unsaturated acid having 4–20 carbon atoms (10–20%) and a copolymer resulting from the polymerization of at least an unsaturated ester and at least an unsaturated acid. The resin concentration generally ranges between about 1–20% by weight of the composition.

In a particular embodiment, the cosmetic resins contained in the compositions according to the invention can have side chains at the end of which is a thiol function.

The cosmetic resins contained in the hair-setting lacquer or lotion compositions of this invention can also be made up of colored polymers, i.e., polymers containing, in their macromolecular chain coloring nuclei which give a particular coloration or shade to the hair. These compositions can also contain direct dyes intended to effect coloring or tinting of the hair. They can also contain ingredients standard to cosmetic compositions intended for fixing the hair in a particular state, such as a penetrating agent, a surfactant, a dye, a perfume or the like.

The cosmetic vehicles that can be used for embodying such types of compositions can be made up of standard mixtures used for making hair-setting lacquers and lotions or again hair dressing compositions.

In accordance with one embodiment, there is thus provided a hair setting lotion composition comprising a lower alkanol or dilute aqueous lower alkanol solution of at least one active compound of Formula I and a cosmetic resin as defined above.

The hair setting lotion, for example, can be made by introducing into a dilute alcohol solution having a concentration of 0 to 70 weight percent alcohol, 1 to 20% and preferably 1 to 3% based on the weight of said composition of a resin as defined above.

This alcohol or dilute alcohol solution of the active compound can also be mixed with a suitable amount of liquified propellant gas under pressure and packaged in an aerosol container to produce a sprayable aerosol hair lacquer composition.

By way of example, an aerosol hair lacquer can be made by introducing 1 to 20, and preferably 1 to 5 weight percent of a resin as defined above in a mixture made up of ¼ to ⅓ by weight of a lower alkanol and ⅔ to ¾ by weight of a liquified propellant gas under pressure. Conventional aerosol propellants such as fluorinated hydrocarbon, including the Freons, can be employed. Representative of such propellants are dichlorodifluoromethane, trichloromonofluoromethane and mixtures thereof. Obviously, other well-known propellants can also be used.

In these hair-setting lotion or hair lacquer compositions the concentration of the active compound generally ranges from 0.5 to 20%, thereby making it possible to treat the hair by subjecting it to a setting operation, this process being essentially characterized by the fact that hair is impregnated with said composition, rolling the hair up on curlers and drying said hair.

The novel cosmetic compositions according to the invention can also take the form of a topically applied shampoo which also contains said active compound in amounts of about 0.5–20 and preferably 1–10 percent by weight. The carrier or vehicle can be water or an aqueous solution of a lower alkanol as described above. In addition, these shampoo compositions, which have a pH of about 3–8, also contain 4–15, preferably 5–7 weight percent, of an anionic, cationic, amphoteric or nonionic detergent.

Anionic detergents include both the soap and non-soap detergents. Examples of suitable soaps are the sodium, potassium, ammonium and alkanol ammonium salts of higher fatty acids ($C_8$–$C_{20}$). Examples of anionic non-soap detergents are alkyl glyceryl ether sulfonates, alkyl sulfates, alkyl ether sulfates, alkyl monoglyceride sulfates or sulfonates, alkyl polyethoxy ether sulfates, alkanolamide sulfonates, alkanolamide sulfates, alkyl monosulfosuccinates, acyl sarcosinates, acyl esters of isethionates, acyl-N-methyl taurines, alkyl benzene sulfonates, alkyl phenol polyethoxysulfonates and condensation products of fatty acids with a protein hydrolyzate. In these compounds the alkyl and acyl moieties can contain 8–20 carbon atoms and they can be used in the form of water-soluble salts such as the sodium, potassium, ammonium and alkanol ammonium salts.

Suitable examples of cationic detergents are long chain quaternary ammoniums, esters of fatty acids and amino-alcohols and polyether amines. Specifically, there can be used dilauryldimethyl ammonium chloride, diisobutyl phenoxyethoxy ethyl dimethylbenzyl ammonium chloride, cetyl trimethyl ammonium bromide, N-cetyl pyridinium bromide and benzethonium chloride, lauryl benzly trimethyl ammonium bromide or chloride, myristyl benzyl trimethyl ammonium bromide or chloride and cetyl benzyl trimethyl ammonium bromide or chloride.

Representative non-ionic detergents are the esters of polyolys and sugars, products of condensation of ethylene oxide on fatty acids, on fatty alcohols, on long chain alkylphenols, on long chain mercaptans, on long chain amides, polyethers of polyhydroxyl fatty alcohols.

Suitable examples of detergents are asparagine derivatives, alkyl dimethyl betaine, alkyl betaamino propionates wherein the alkyl moiety contains 10–20 carbon atoms, basic quaternary ammonium compounds derived from 2-alkyl substituted imidazoline, condensation products of monochloroacetic acid and imidazoline and compounds of the formula

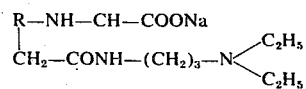

wherein R is a radical derived from fatty acids of copra and radicals ($C_8$–$C_{20}$) derived from tallow.

The shampoo compositions as defined above can also contain other usual cosmetic ingredients, such as perfumes, dyes, and bactericides or fungicides, when the shampoos also have an anti-dandruff action. They can also contain thickeners such as alkanolamides of fatty acids, derivatives of cellulose, for example, carboxymethyl cellulose and hydroxymethyl cellulose, long chain polyol esters and natural gums to provide a cream or gel.

These shampoo compositions can also be in the form of a powder which can be applied either to the wet hair, or be solubilized in a predetermined volume of water before washing the hair.

The shampoo compositions can also include conventional hair dyes to tint or color the hair.

In use these shampoo compositions are applied to the hair and scalp generally in amounts of 10–20 cc to combat the greasy and unaesthetic appearance of the hair, and dandruff, optionally before wetting the hair. The scalp is massaged for one to several minutes and the hair is rinsed. Generally a satisfactory result is obtained by weekly shampooing, which makes it possible to reduce and, in certain cases, to eliminate the greasy appearance of the hair, while also assuring normal upkeep of the hair.

Yet another topicaly applied composition including the active compounds of the present invention is a formulation for use in effecting a permanent wave or deformation of hair exhibiting a greasy or unaesthetic appearance, which not only provides an acceptable waving of the hair but also essentially eliminates the greasy appearance thereof at the same time.

As is known, the permanent deformation of the hair can be achieved either in one stage or two stages.

When the permanent deformation of the hair is achieved in two stages, the active compounds of Formula I above can be present, either in the reducing composition for use during the first stage of the permanent waving operation or in an oxidizing or neutralizing composition for use during the second stage of the permanent waving operation. When the permanent deformation of the hair is achieved in a single stage, a self-neutralizing composition contains, in association with the self-neutralizing agents, the active compounds of Formula I above.

In one embodiment of the use of such permanent wave formulations, the hair is permanently waved by applying to the hair wound on curlers during the first stage, i.e. during the reducing stage, a cosmetic composition comprising a mixture of a reducing agent and the active compound of this invention, permitting the composition to remain on the hair for a time sufficient to alter the disulphide bonds of the keratin of the hair, generally about 10 to 40 minutes, thoroughly rinsing the hair to remove residual reducing agent and applying in the second stage, i.e., during the neutralization stage, an oxidizing or neutralizing agent to reform the disulphide bonds of the keratin of the hair.

In another embodiment of using these permanent wave formulations the hair is permanently waved by applying to the hair wound on curlers during the first stage, i.e., during the reducing stage, a reducing agent, permitting the composition to remain on the hair for a time sufficient to alter the disulphide bonds of the keratin of the hair, generally about 10 to 40 minutes, thoroughly rinsing the hair to remove residual reducing agent and applying in the second stage, i.e., during the neutralization stage, a cosmetic composition comprising a mixture of an oxidizing or neutralizing agent and the active compound of this invention whereby the disulphide bonds of the keratin of the hair are reformed.

In an alternative procedure the hair is permanently waved in a single stage operation by impregnating the hair wound on curlers with a cosmetic composition comprising a mixture of a thiol reducing agent for altering the disulphide bonds of the keratin of the hair, an organic disulphide and the active compound of the present invention, the molar ratio of said organic disulphide to said thiol being greater than 1, and as high as about 20, permitting the compositin to remain on the hair for a time sufficient to induce a permanent wave therein, generally about 10 to 40 minutes, and unwinding the hair from the curlers. Conventional separate neutralization operations are not required in the practice of this embodiment of the invention.

The active compound of this invention used in these permanent wave formulations is admixed with a conventional reducing agent and is present in the resulting mixture in amounts between 0.5–20 weight percent. The pH of this cosmetic composition is preferably between 3 and 9.5. Conventional reducing agents employed are advantageously those organic thiols which are generally used to perform the first stage of a permanent waving operation. Representative thiols include thioglycolic acid, ammonium thioglycolate, thioglycerol, thiolactic acid, thioglycolic amide or hydrazide or the like.

Conveniently, and also in accordance with the present invention, the reducing composition is a two-package composition, the first package containing a thiol reducing agent as described above and the second package containing the active compound of this invention in amounts such that when the contents of the two packages are mixed together, preferably just before initiation of the reducing operation, the resulting reducing composition contains said active compound in amounts of about 0.5–20 weight percent of the reducing composition.

Alternatively, the said active compound is admixed with a conventional neutralizing or oxidizing agent and is present in the resulting mixture in amounts between 0.5–20 and preferably between 1–10 weight percent of the total. Conventional neutralizing agents employed include, for instance, hydrogen peroxide, sodium or potassium bromate, sodium perborate or percarbonate and the like.

Conveniently also, the neutralizing composition is a two-package composition, the first package containing the neutralizing agent as described above and the second package containing said active compound also as defined above in amounts such that when the contents of the two packages are mixed together, preferably just before initiation of the neutralizing operation, the resulting neutralizing composition contains the active compound in amounts of about 0.5–20 weight percent of the neutralizing composition.

As a further alternative, the active compound is admixed with a single stage permanent hair waving agent, and is present in the resulting mixture in amounts between 0.5–20, and preferably between 1–10 weight percent of the total. Conventional single stage permanent hair waving agents can be employed and include a mixture of an organic disulfide and a thiol, the mol ratio of the disulfide to the thiol being greater than 1.

Suitable thiols include thioglycolic acid, glycol thioglycolate, glycerol thioglycolate, β-mercaptoethanol, N-carboxymethyl-mercaptoacetamide, glycol thiolactate and the like.

As the organic disulphides there can be used the disulphides of the thiols set forth in the preceding paragraph. For instance, glycol dithiodiglycolate, glycerol dithioglycolate, glycol dithiodilactate, dithiodiethanol and N-carboxymethyldithioacetamide and be employed. Additional ingredients can include ammonia, water, urea and lower alkanols in conventionally employed amounts. The pH of the single stage permanent hair waving composition ranges between about 8–10, preferably about 8.5–9.5.

Again, conveniently, the single stage permanent hair waving composition is a two-package composition, the first package containing the single stage permanent hair waving agent and the second package containing the active compound, as defined above, in amounts such that when the contents of the two packages are mixed together, preferably just before use, the resulting permanent hair waving composition contains the active compound in amounts of about 0.5–20 weight percent of the total mixture.

As will be recognized, these permanent wave formulations can also include other additives conventionally employed such as penetrating agents, surfactants, dyes or perfumes and can be admixed with conventional vehicles such as water, lower alkanols and their mixtures as defined above. Further, they can also be provided in the form of a solution, a foam, a cream or gel or they can be provided in the form of a sprayable aerosol especially when the cosmetic vehicle is water, lower alkanol or their mixtures. The sprayable aerosol can include an effective amount of a liquified gas under pressure, such as a fluorochlorinated hydrocarbon, for instance the Freons 11, 12 and 114 and their mixtures.

The novel compositions making it possible to perform a permanent deformation of the hair can also contain the standard ingredients of cosmetic compositions intended to perform permanents, such as penetrating agents, surfactants, dyes, perfumes.

In yet another embodiment of the present invention, a dermal lotion composition can be prepared which contains the active combound defined above in amounts of about 0.5–20 weight percent of the total, together with a suitable cosmetic vehicle. This composition is applied to the skin to improve its appearance when it presents a greasy appearance.

Such dermal lotion compositions are preferably in the form of creams, milks, gels, dermatological cakes or aerosol foams. These compositions can also be in the form of aqueous or dilute alcohol solutions. Further, they can contain conventional components employed in beauty creams for the face, such as fatty bodies, emulsifiers, preservatives, perfumes, dyes and waxes. Additionally, they can also contain colored pigments to dye or color the skin and to mask skin defects.

These dermal lotion compositions can also contain bactericides or fungicides, such as hexachlorophene, quaternary ammonium compounds such as tetradecyltrimethyl ammonium bromide and the compounds described in Luxembourg Pat. Nos. 59,405 and 60,384.

In accordance with another embodiment of the present invention, there is provided a composition and method for eliminating a greasy and unaesthetic appearance of the hair which comprises orally administering to a human being having hair so characterized a composition comprising an ingestible carrier admixed with, as a non-toxic active component, the active compound as defined hereinbefore.

These novel compositions can be in liquid or solid form and when the liquid form is desired, the active compound can be dissolved in an alimentary liquid, such as water or an aqueos solution of a non-toxic lower alkanol, such as ethanol. These liquid orally administered compositions generally contain about 0.5–20 percent by weight of the active compound, the remainder being essentially the ingestible carrier.

The orally administered compositions can also be provided as a solid, in the form of granules, pills, tablets or lozenges and in this form the active compound is generally present in amounts of about 0.5–20 weight percent, the remainder being essentially a solid ingestible carrier or excipient. Examples of suitable excipient or carrier formulations can be found in U.S. Pat. No. 2,888,380.

The active compounds of the present invention are non-toxic and therefore the specific amounts orally administered can be left to the discretion of the user. However, it has been found appropriate to use these orally administered compositions for successive periods of 15 days with a 15 day interruption at a dosage of about 100 mg per 24 hour period.

There will now be described, by way of illustration, several examples of preparation of the active compounds and several examples of composition according to the invention.

EXAMPLES OF PREPARATION

Example 1

Preparation of trans-3,4-thiolannediol

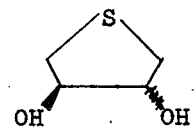

A solution of 240 g of nonahydrated sodium sulfide in 2 liters of water is added during a 2 hour period to 159 g of DL 1,4-dichloro 2,3-butanediol in a liter of ethanol. The temperature is kept between 20° and 30°C. After 24 hours, a check is made to see that there is no longer any sulfide in solution by the nitroprussiate test. The solution is then treated with animal black and filtered. The filtrate is concentrated under vacuum at a temperature below 50°C and the residue is extracted with boiling ethanol. The ethanol solution, after filtering, is concentrated. The oily residue (96.2 g) crystallizes by cooling. The product obtained can be crystallized in a chloroform-benzene-acetonitrile mixture in the form of white crystals melting at 69°–70°C. Chromatography on a thin polyamide layer: Rf 0.10 (chloroform).

Analysis:
Calculated %: C, 39.96; H, 6.72; S, 26.65. Found: C, 39.91; H, 6.64; S, 26.49.

Example 2

Preparation of cis-3,4-thiolannediol

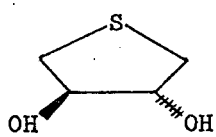

To a solution of 248 g of meso 1,4-dibromo 2,3-butanediol in two liters of ethanol, is added over a 2 hour period at a temperature between 20° and 30°C, a solution of 240 g of nonahydrated sodium sulfide. The mixture is stirred for an hour then concentrated under vacuum at a temperature less than 25°C by means of a rotary evaporator. The residue is then extracted with boiling ethanol and filtered. The ethanol solution is then concentrated. Thus an oil is obtained which crystallizes slowly. The white product obtained (112 g) crystallizes in chloroform without changing melting point: F = 70°. Chromatography on a thin polyamide layer: Rf = 0.50 (chloroform).

Analysis C₄H₈O₂S:
Calculated %: C, 39.96; H, 6.72; S, 26.65.
Found: C, 40.03; H, 6.64; S, 26.46.

Example 3

Preparation of trans 3,4-thiolannediol S-oxide

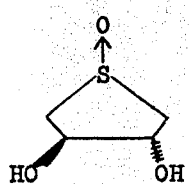

There is cooled and kept at 0°–2°C a solution of 120 g of trans 3,4-thiolannediol in a liter of water. Then there are added in eight hours 100 cc of 30% hydrogen peroxide diluted in 500 cc of cold water. The solution is left initially for 2 days at 0°C, then for 3 days at ambient temperature, before being evaporated to dryness at a temperature below 50°C. The residue is dissolved by ethanol and filtered. 129 g of white crystals melting at 162° are collected. Chromatography on a thin alumina layer: Rf = 0.15–0.30 (butanol-ammonia).

Analysis C₄H₈O₂S:
Calculated %: C, 35.28; H, 5.92; S, 23.54.
Found: C, 35.19; H, 5.85; S, 23.50.

Example 4

Preparation of cis 3,4-thiolannediol S-oxide

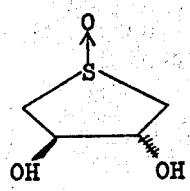

By applying the above conditions to cis 3,4-thiolannediol, 119.5 g of white crystals are obtained, which are a mixture of stereoisomers with a melting point F = 88°–98°. Chromatography on a thin layer of alumina: Rf = 0–0.15 (butanol-ammonia).

Example 5

Preparation of trans 3,4-thiolannediol S-dioxide

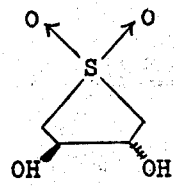

24 g of trans 3,4-thiolannediol are put in solution in 200 ml of glacial acetic acid and 20 ml of water. With stirring there are introduced in 3 hours at a temperature of 40°–50°C, 66 ml of 30% hydrogen peroxide in admixture with 100 ml of acetic acid. The temperature is held at 60°C for 24 hours by heating. The reaction mixture is then concentrated at a temperature below 40°C, then the residue is washed several times with water to eliminate the peroxides and again evaporated under vacuum at a temperature always under 40°C. Thus there is obtained a white solid which is dissolved in 50 ml of ethanol. After filtering the crystallized product, it is dried in an oven. There are obtained 24 g of a dry product (78%) with a melting point of 157°C.

By recrystallization in the ethanol-acetone mixture the melting point is stabilized at 158°–159°C.

Example 6

Preparation of cis 3,4-thiolannediol S-dioxide.

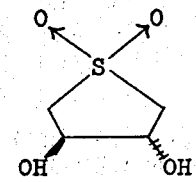

After dissolving 118 g of 3-sulfolene in two liters of water, there is introduced in 2 hours a solution of 125 g of crystallized KMnO₄ and of 192 g of SO₄Mg.7 H₂O in 2.5 liters of water while keeping the reaction mixture temperature at 0°C. The mixture is then kept at 0°C for an hour. Subsequently, 420 ml of 30% sodium bisulfite are introduced and acidified with 50% SO₄H₂ to pH 7.

The resulting mixture is then concentrated to dryness with a rotary evaporator, keeping the temperature below 50°C.

Thereafter, the residue is dissolved with acetonitrile, filtered, concentrated and allowed to crystallize. There are thus obtained after filtering, 52 g of a product exhibiting a melting point of 129°C. After recrystallization in acetonitrile the melting point stabilizes at 129°–130°C.

Trans 3,4-thiolannediol S-dioxide can, in the same way, be prepared from 3-sulfolene by using as the oxidizing agent a mixture of formic acid and hydrogen peroxide (yield 49%). Melting point (after recrystallization in acetonitrile) = 158°–159°C.

EXAMPLES OF COMPOSITION AND USE

Example 7

A men's hair dressing lotion is prepared by mixing:

| | |
|---|---|
| Trans 3,4-thiolannediol S-oxide | 0.75 g |
| Dimethylhydantoin formol resin | 0.5 g |
| Dimethyl-dilaurylammonium chloride | 0.5 g |
| Perfume | 0.1 g |
| Alcohol (isopropanol) | 50 cc |
| Water, q.s.p. | 100 cc |

After the application of this lotion to greasy hair, a general improvement of the appearance of the hair is noticed.

Example 8

A capillary composition is prepared by mixing together:

| | |
|---|---|
| Cis 3,4-thiolannediol | 1.5 g |

-continued

| | |
|---|---|
| Distilled perfumed water | 100 cc | to which is then added:

| | |
|---|---|
| "Carbopol", carboxyvinyl polymer, (Merck Index Ed. 1968, p.210) | 1.25 g |

The resulting mixture is alkalinized by a drop of ammonia to obtain a pH between 8.0 and 8.2.

A gel is thus obtained which when applied to greasy hair presenting dandruff, improves the general state of the hair.

Example 9

A capillary lotion according to the invention is prepared by dissolving 20 g of cis 3,4-thiolannediol S-dioxide in 100 cc of 50% dilute solution of ethanol.

This lotion when applied to greasy hair essentially eliminates the unaesthetic appearance of the hair.

Example 10

A liquid shampoo is prepared according to the invention by mixing the following compounds:

| | |
|---|---|
| Sodium lauryl sulfate oxyethylenated with 2.2 moles of ethylene oxide | 9 g |
| Sodium mono lauryl sulfosuccinate | 1 g |
| Polyethylene glycol distearate | 2 g |
| Lauryl diethanolamide | 2 g |
| Trans 3,4-thiolannediol S-oxide | 2 g |
| Perfume | 0.3 g |
| Lactic acid, q.s.p. | pH = 6.5 |
| Water, q.s.p. | 100 g |

Weekly shampooing imparts to greasy hair a normal, aesthetic appearance.

Example 11

A cream shampoo is made by mixing the following components:

| | |
|---|---|
| Sodium lauryl sulfate | 10 g |
| Condensation product of copra fatty acids and methyltaurine, a paste marketed under the name "Hostapon C.T.", having the formula R—CON—CH$_2$—CH$_2$—SO$_3$Na  \|  CH$_3$ wherein R represents the copra radical C$_5$ to C$_{17}$ | 45 g |
| Lauryl monoethanolamide | 2 g |
| Glycerol monostearate | 4 g |
| Trans 3,4-thiolannediol | 2 g |
| Lactic acid, q.s.p. | pH = 6.6 |
| Perfume | 0.2 g |
| Water, q.s.p. | 100 g |

As in the preceding example, excellent results are obtained by weekly application.

Example 12

An anti-dandruff powder shampoo is made by mixing the following:

| | |
|---|---|
| Sodium lauryl sulfate | 50 g |
| Condensation product of copra fatty acids and sodium isethionate, marketed under the name of "Hostapon K.A." having the formula: RCOO—CH$_2$—CH$_2$—SO$_3$Na wherein R represents the copra radical C$_5$ to C$_{17}$ | 41 g |
| S-(N-oxypyridyl-2)1-cysteine | 6 g |
| Cis 3,4-thiolannediol S-dioxide | 2 g |
| Perfume | 1 g |

Just before use, the above powder is dissolved in 10 times its weight of water, the solution then being applied to the hair and scalp. A general improvement of the appearance of the hair is thus obtained.

Example 13

A dye shampoo for greasy hair is made by preparing a mixture having the following composition:

| | |
|---|---|
| Trans 3,4-thiolannediol | 5 g |
| Ammonium lauryl sulfate oxyethylenated with 2 moles of ethylene oxide | 250 g |
| Paratoluylenediamine | 10 g |
| Metadiamino anisol sulfate | 0.5 g |
| Resorcin | 5 g |
| Metaaminophenol | 1.5 g |
| Paraaminophenol | 1 g |
| Tetracetic acid ethylene diamine | 3 g |
| 40% sodium bisulfite | 15 g |
| Water, q.s.p. | 1000 g |

This product is then mixed with 1000 g of 20 volume hydrogen proxide and hair containing 80% white hair is then impregnated with the resulting mixture. A brown coloration and a reduction of the greasy appearance of the hair are obtained.

Example 14

The first stage of a permanent waving operation for greasy hair is performed with a reducing composition containing:

| | |
|---|---|
| Ammonium thioglycolate | 9.5 g |
| Wax Sipol AO (mixture of 30% cetyl alcohol and 70% stearic alcohol, polyoxyethylenated with 33 moles of ethylene oxide) | 0.8 g |
| Ammonia solution, q.s.p. | 0.7 N |
| Water, q.s.p. | 100 g |

With the hair thus impregnated with the above composition and up in curlers, a setting is performed with the following composition:

| | |
|---|---|
| Sodium bromate | 18 g |
| Cis 3,4-thiolannediol | 0.5 g |
| Water, q.s.p. | 100 g |

After the hair is rinsed, taken down and dried, a permanent is obtained with a good holding, the hair being much less greasy than before.

Example 15

The first stage of a permanent waving operation for greasy hair is performed with the composition in two parts described below:

The first part contains:

| | |
|---|---|
| Ammonium thioglycolate | 9.5 g |
| Monoethanolamine, q.s.p. | 0.65 N solution |
| Ammonium lauryl sulfate | 0.5 g |
| Water, q.s.p. | 100 cc |

The second part is made up of:

| | |
|---|---|
| Trans 3,4-thiolannediol S-oxide | 1 g |

The second part is dissolved in the reducing composition constituting the first part and the first stage of a permanent waving operation is performed with this composition.

Example 16

A masking cream, intended for treating greasy skin, is prepared by mixing the following components:

| | |
|---|---|
| Trans 3,4-thiolannediol S-oxide | 1.5 g |
| S-(N-oxypryidyl-2)1-cysteine | 2 g |
| Titanium oxide | 10 g |
| Red iron oxide | 0.3 g |
| Yellow iron oxide | 0.2 g |
| Brown iron oxide | 0.4 g |
| Chestnut iron oxide | 0.2 g |
| Cetyl-stearyl alcohol oxyethylenated with 15 moles ethylene oxide | 7 g |
| Silicone oil (dimethylpolysiloxane having a viscosity of 20–22° at room temperature) | 1 g |
| Polyglycol stearate (M.W. polyglycol-400) | 6 g |
| Propyl parahydroxybenzoate | 0.20 g |
| Water, q.s.p. | 100 g |

Application of this composition to the skin provides a less greasy and more normal appearance.

Example 17

An aerosol foam is prepared for greasy skin by mixing in an aerosol bomb the following ingredients:

| | |
|---|---|
| Cis 3,4-thiolannediol S-oxide | 2.5 g |
| "Carbopol", carboxyvinyl polymer (Merck Index E. 1968, p.210) | 25 g |
| Mg ethoxylauryl sulfate | 8 g |
| Glycerin | 10 g |
| Ammonia | 0.2 g |
| Hexachlorophene | 2 g |
| Water, q.s.p. | 100 g |

88 g of the solution described above is packaged in an aerosol bomb with 12 g of difluorodichloromethane. This foam, regularly applied, imparts to the skin a normal appearance.

Example 18

An anionic anti-dandruff liquid shampoo is prepared by mixing the following components:

| | |
|---|---|
| Trans 3,4-thiolannediol | 1 g |
| Cis 3,4-thiolannediol | 1 g |
| Technical (100%) sodium lauryl sulfate oxyethylenated with 2.2 moles ethylene oxide | 7 g |
| Copra diethanolamine | 2 g |
| "Carbopol", carboxyvinyl polymer (Merck Index Ed. 1968, p.210) | 0.9 g |
| Hydroxymethyl cellulose | 0.4 g |
| Zinc chelate of S-(2-pyridyl N-oxide) 1-cysteine | 2 g |
| Perfume | 0.5 g |
| Dye (F.D.C. Green No. 3 of the empirical formula $C_{37}H_{34}N_2O_{10}S_3Na_2$) | 0.1 g |
| Water, q.s.p. | 100 g |

This shampoo is an opaque liquid suspension having a pH of 7–7.5.

Weekly washing of the head with this shampoo substantially eliminates dandruff without imparting a greasy appearance to the hair. The shampoo is applied twice with intermediate rinsing, in sufficient amount to obtain the formation of a foam upon second application.

Example 19

An anti-dandruff anionic liquid shampoo is prepared by mixing the following components:

| | |
|---|---|
| Technical (100%) triethanolamine lauryl sulfate (100%) | 9 g |
| Copra diethanolamide | 4 g |
| "Veegum F", (purified colloidal magnesium silicate) | 5 g |
| Sodium chloride | 3 g |
| Trans 3,4-thiolannediol S-dioxide | 2 g |
| 2-pyridine thiolate of zinc N-oxide | 2 g |
| Carboxymethyl cellulose | 0.3 g |
| Perfume | 0.5 g |
| Dye (F.D.C. Green No. 3 of the formula $C_{37}H_{34}N_2O_{10}S_3Na_2$) | 0.1 g |
| Water, q.s.p. | 100 g |

This shampoo is in the form of an opaque, liquid suspension, with a pH 7–7.5 and when applied under the conditions of Example 18, also gives comparably good results in the cases of hair and scalp exhibiting dandruff and a greasy appearance.

Example 20

An anionic anti-dandruff cream shampoo is made by mixing the following components:

| | |
|---|---|
| Trans 3,4-thiolannediol S-oxide | 2 g |
| Technical (100%) sodium lauryl sulfate | 10 g |
| Copra monoethanolamide | 5 g |
| Glycerol monostearate | 6 g |
| Lanolin | 1 g |
| Zinc chelate of S-(2-pyridyl N-oxide) 1-cysteine | 2 g |
| Dye (F.D.C. Green No. 3 of the empirical formula $C_{37}H_{34}N_2O_{10}S_3N_2$) | 0.1 g |
| Perfume | 0.5 g |
| Water, q.s.p. | 100 g |

This shampoo when applied according to the conditions of Example 18 also gives comparably good results in the case of hair and scalp exhibiting dandruff and a greasy appearance.

Example 21

A foaming gel for greasy skin is prepared by mixing the following components:

| | |
|---|---|
| Cis 3,4-thiolannediol | 7.5 g |
| "Carbopol", carboxyvinyl polymer (Merck Index Ed. 1968, p.210) | 25 g |
| Magnesium ethoxylauryl sulfate | 8 g |
| Glycerin | 10 g |
| Ammonia | 0.2 g |
| Zinc chelate of S-(2-pyridyl N-oxide) 1-cysteine | 2 g |
| Water, q.s.p. | 100 g |

This gel, when applied to the skin, significantly reduces its greasy appearance.

Example 22

A cake for greasy skin is prepared by mixing the following components:

| | |
|---|---|
| Trans 3,4-thiolannediol S-dioxide | 1 g |
| Esters of sodium isethionate and copra fatty acids sold under the tradename "Igepon A", and having the formula R—COO—CH$_2$—CH$_2$—SO$_3$—Na, wherein R = fatty acid derivatives having from 12 to 18 carbon atoms | 74 g |
| Lanolin derivatives sold by Croda under the tradename "Super | |

-continued

| | |
|---|---|
| Hartolan" and lecithin | 23 g |
| S-(2-pyridyl N-oxide)1-cysteinate of methyl | 2 g |

This cake, when regularly applied to a greasy skin, significantly reduces its greasy appearance.

Example 23

Lozenges, for oral consumption, are prepared, each having the following composition:

| | |
|---|---|
| Trans 3,4-thiolannediol S-oxide | 50 mg |
| Lactose | 300 mg |
| Gum arabic powder | 100 mg |
| Simple syrup | 500 mg |

These lozenges, taken at a rate of two per day, effect a substantial regression of the greasy appearance of the hair.

Essentially similar effective results are obtained when the active compound in these lozenges is replaced by cis or trans 3,4-thiolannediol, cis or trans 3,4-thiolannediol-S-dioxide or cis 3,4-thiolannediol-S-oxide.

Example 24

The following composition for oral administration in the form of drops is prepared by mixing

| | |
|---|---|
| Cis 3,4-thiolannediol | 20 g |
| Glycerin | 40 g |
| Ethyl alcohol | 30 g |
| Water, q.s.p. | 100 g |
| Lemon tincture (sufficient for flavor) | |

Oral administration of this composition at a rate of 10 drops per day for 15 days to a person having greasy hair substantially eliminates the greasy appearance of the hair and considerably improves the appearance of the scalp and hair.

Essentially similar effective results are obtained when the cis 3,4-thiolannediol in these drops is replaced with trans 3,4-thiolannediol, cis or trans 3,4-thiolannediol-S-oxide or cis or trans 3,4-thiolannediol-2-dioxide.

Example 25

Chewable pellets having the following composition, are prepared:

| | |
|---|---|
| Trans 3,4-thiolannediol S-dioxide | 12.5 g |
| Saccharose | 200 g |
| Lemon syrup | 50 g |

These pellets, administered at a rate of 1 teaspoon twice per day, effect a notable regression or substantial elimination of the greasy appearance of the hair.

Essentially similar effective results are achieved when the trans 3,4-thiolannediol-S-dioxide in these pellets is replaced by cis or trans 3,4-thiolannediol, cis or trans 3,4-thiolannediol-S-oxide or cis 3,4-thiolannediol-S-dioxide.

What is claimed is:

1. A process to combat dandruff and to eliminate a greasy appearance of the hair and scalp of a person having hair and scalp so characterized comprising topically applying to the hair an effective amount of a composition comprising a nontoxic carrier comprising a member selected from the group consisting of water and a dilute aqueous lower alkanol solution and an active compound of the formula

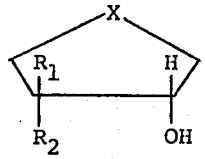

wherein
X is selected from the group consisting of S, SO and $SO_2$, and
$R_1$ is selected from the group consisting of
a. H, in which case $R_2$ is OH, and
b. OH, in which case $R_2$ is H,
said active compound being present in an amount effective to combat dandruff and to eliminate said greasy appearance of the hair and scalp.

2. The process of claim 1 wherein said active compound is selected from the group consisting of
cis and trans 3,4-thiolannediol,
cis and trans 3,4-thiolannediol S-oxide, and
cis and trans 3,4-thiolannediol S-dioxide.

3. The process of claim 1 wherein said composition contains 0.5 – 20 weight percent of said active compound and said composition is applied to the hair in an amount of 15 – 20 cc by massaging.

4. A composition to combat dandruff and to eliminate a greasy appearance of the hair comprising
1. 0.5 – 20 percent by weight of an active compound of the formula

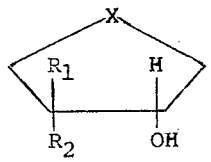

wherein
X is selected from the group consisting of —S—, —SO— and —$SO_2$—, and
$R_1$ is selected from the group consisting of
a. H, in which case $R_2$ is OH and
b. OH, in which case $R_2$ is H;
2. from 1 to 20 weight percent of a cosmetic film forming resin having a molecular weight ranging from about 10,000 – 70,000; and
3. a carrier selected from the group consisting of water and a dilute aqueous lower alkanol solution having a concentration of 0 – 70 weight percent of said lower alkanol.

5. The composition of claim 4 wherein X is —S—.
6. The composition of claim 4 wherein X is —SO—.
7. The composition of claim 4 wherein said active compound is present in an amount of 1 – 10 weight percent.

8. A composition to combat dandruff and to eliminate a greasy appearance of the hair comprising
1. 0.5 – 20 weight percent of an active compound of the formula

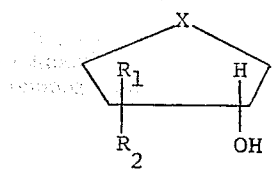

wherein
X is selected from the group consisting of —S—, —SO— and —SO$_2$—, and
R$_1$ is selected from the group consisting of
  a. H, in which case R$_2$ is OH and
  b. OH, in which case R$_2$ is H;
2. from 4 – 15 weight percent of a detergent selected from the group consisting of an anionic, cationic, amphoteric and nonionic detergent; and
3. a carrier selected from the group consisting of water and a dilute aqueous lower alkanol solution said composition having a pH between 3 – 8.

9. The composition of claim 8 wherein X is —S—.

10. The composition of claim 8 wherein X is —SO—.

11. The composition of claim 8 wherein said active compound is present in an amount of 1 – 10 weight percent.

12. The composition of claim 8 wherein said detergent is present in an amount of 5 – 7 weight percent.

* * * * *